(12) United States Patent
Paik et al.

(10) Patent No.: US 9,618,490 B2
(45) Date of Patent: Apr. 11, 2017

(54) GAS SENSOR PACKAGE

(71) Applicant: LG INNOTEK CO., LTD., Seoul (KR)

(72) Inventors: Jee Heum Paik, Seoul (KR); Yun Mi Bae, Seoul (KR); Go Eun Hwang, Seoul (KR)

(73) Assignee: LG Innotek Co., Ltd., Seoul (KR)

( * ) Notice: Subject to any disclaimer, the term of this patent is extended or adjusted under 35 U.S.C. 154(b) by 191 days.

(21) Appl. No.: 14/503,480

(22) Filed: Oct. 1, 2014

(65) Prior Publication Data

US 2015/0090002 A1    Apr. 2, 2015

(30) Foreign Application Priority Data

Oct. 1, 2013  (KR) .......................... 10-2013-0117299
Oct. 22, 2013  (KR) .......................... 10-2013-0126035

(51) Int. Cl.
*G01N 33/00* (2006.01)
*G01N 27/12* (2006.01)
(Continued)

(52) U.S. Cl.
CPC ....... *G01N 33/0027* (2013.01); *B81B 7/0061* (2013.01); *H01C 7/04* (2013.01); *B81B 2201/0214* (2013.01); *B81B 2207/012* (2013.01); *G01N 27/128* (2013.01); *G01N 2033/0095* (2013.01); *H01L 24/16* (2013.01); *H01L 2224/05568* (2013.01); *H01L 2224/05573* (2013.01); *H01L 2224/16227* (2013.01); *H01L 2224/81411* (2013.01); *H01L 2224/81439* (2013.01); *H01L 2224/81444* (2013.01); *H01L 2924/00014* (2013.01);
(Continued)

(58) Field of Classification Search
CPC .. G01N 33/00; G01N 33/0027; G01N 27/128; G01N 2033/0095; H01C 7/04; H01L 24/16; H01L 2224/16227; H01L 2224/81411; H01L 2224/81439; H01L 2224/81444; H01L 2924/10157; H01L 2924/10158; H01L 2924/15311; H01L 2924/00014
See application file for complete search history.

(56) References Cited

U.S. PATENT DOCUMENTS 6,140,144 A    10/2000  Najafi et al.
6,351,390 B1    2/2002  Mayer et al.
(Continued)

FOREIGN PATENT DOCUMENTS

DE    10 2008 040 187 A1    1/2010
EP    1 103 808 A2    5/2001
(Continued)

OTHER PUBLICATIONS

European Search Report dated Apr. 8, 2015 issued in Application No. 14187183.0.
(Continued)

*Primary Examiner* — Nguyen Ha
(74) *Attorney, Agent, or Firm* — KED & Associates LLP

(57) ABSTRACT

Provided is a gas sensor package, including: a first substrate including a gas inflow hole; and a gas sensing element mounted to the first substrate and including a gas sensing portion disposed to correspond to the gas inflow hole.

9 Claims, 7 Drawing Sheets

(51) Int. Cl.
*H01C 7/04* (2006.01)
*B81B 7/00* (2006.01)
*H01L 23/00* (2006.01)

(52) U.S. Cl.
CPC .............. *H01L 2924/10157* (2013.01); *H01L 2924/10158* (2013.01); *H01L 2924/15311* (2013.01)

(56) References Cited

U.S. PATENT DOCUMENTS

| | | | |
|---|---|---|---|
| 9,017,612 B2* | 4/2015 | Tsukabayashi | G01N 27/16 422/83 |
| 2010/0039779 A1* | 2/2010 | Mitchell | H05K 1/092 361/739 |
| 2015/0075257 A1* | 3/2015 | Paik | G01N 33/0042 73/31.05 |
| 2015/0075258 A1* | 3/2015 | Paik | G01N 27/041 73/31.06 |
| 2015/0198551 A1* | 7/2015 | Jun | H01L 23/10 204/431 |

FOREIGN PATENT DOCUMENTS

| | | | | |
|---|---|---|---|---|
| JP | 2010085339 A | * | 4/2010 | ............. G01B 27/16 |
| JP | 2012-098234 A | | 5/2012 | |
| JP | 2012098234 A | * | 5/2012 | ............. G01N 27/12 |
| WO | WO 87/00634 A1 | | 1/1987 | |

OTHER PUBLICATIONS

European Search Report dated Jan. 9, 2015 issued in Application No. 14187183.0.

* cited by examiner

GAS SENSOR PACKAGE

CROSS-REFERENCE TO RELATED APPLICATIONS

This application claims priority under 35 U.S.C. §119 to Korean Patent Application Nos. 10-2013-0117299, filed on Oct. 1, 2013, and 10-2013-0126035, filed on Oct. 22, 2013, whose entire disclosures are hereby incorporated by reference.

BACKGROUND OF THE INVENTION

1. Field

Embodiments of the present application relate to a gas sensor package.

2. Background

A gas sensor is needed to have characteristics, such as speed showing how fast the gas sensor can respond to a situation, sensibility which can respond to the detection of gas in spite of the detection of a small amount of the gas, durability showing how long the gas sensor can operate, economic efficiency showing that the sensor can be used by consumers without burdens, and the like. In order for the gas sensor to be combined with an existing semiconductor process technology, the gas sensor should have characteristics of the easiness of integration and enumeration. A home gas leakage alarm made of tin oxide (SnO2) as a material has come into wide use as a practical gas sensor. The gas sensor is divided into a semiconductor type using a change of resistance values according to a change in the amount of gas and an oscillator type using a change in an oscillation frequency generated when gas is absorbed onto an oscillator, which oscillates with a predetermined frequency. Most of the gas sensors have been used as the semiconductor type gas sensors having simple circuits and showing a stable thermal property at room temperature.

In general, a gas sensor has a package structure in which a gas sensing material or a sensing chip is mounted to the gas sensor, and should have a separate cap member for protecting an upper surface of the gas sensing material or the sensing chip, and a mesh-shaped member formed of minute nets is provided on an upper surface of the cap member so as to allow the ventilation of gas.

In this gas sensing package for sensing gas, a height of an upper structure is increased due to the cap member and the mesh-shaped member, and an entire size of the gas sensing package is further increased up to several times to dozens of times than that of a sensor chip because a wire bonding method is used when the sensor chip is connected to an electrode part. Due to this, there is a limit to implement miniaturization of the gas sensor.

BRIEF DESCRIPTION OF THE DRAWINGS

The embodiments will be described in detail with reference to the following drawings in which like reference numerals refer to like elements wherein.

DETAILED DESCRIPTION OF THE INVENTION

Figure 1:
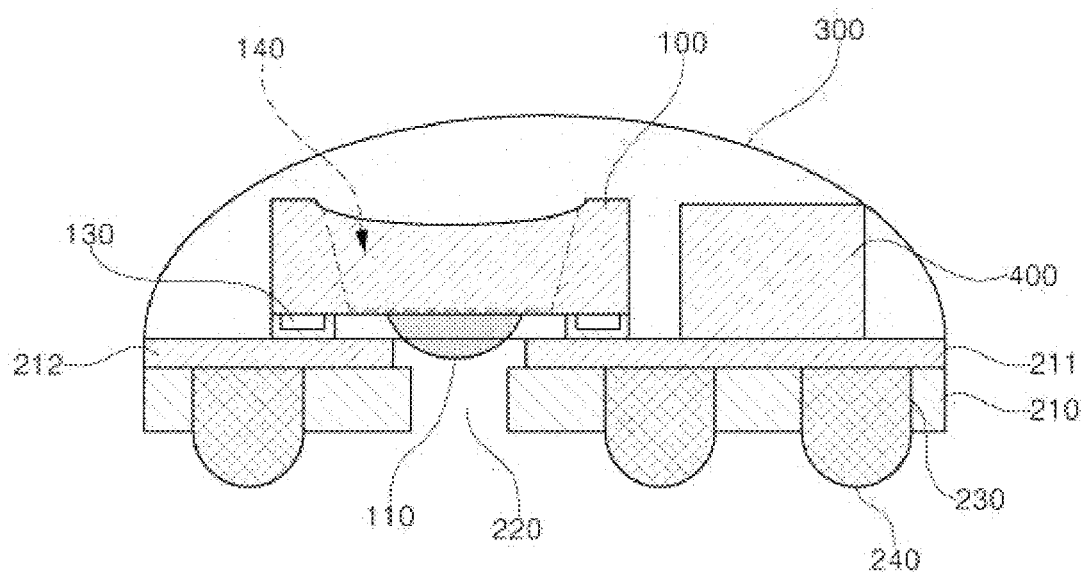
FIGS. 1 and 2 are cross-sectional views of main portions of a gas sensing package according to an embodiment of the present application.

Hereinafter, the configurations and operations according to embodiments of the present application will be described in detail with reference to the accompanying drawings. The present application may, however, be embodied in different forms and should not be construed as limited to the embodiments set forth herein. In the explanation with reference to the accompanying drawings, regardless of reference numerals of the drawings, like numbers refer to like elements through the specification, and repeated explanation thereon is omitted. Terms such as a first term and a second term may be used for explaining various constitutive elements, but the constitutive elements should not be limited to these terms. These terms is used only for the purpose for distinguishing a constitutive element from other constitutive element.

The embodiments of the present application will now be described more fully hereinafter with reference to the accompanying drawings and examples. It will also be understood that when an element is referred to as being "on" another element, substrate, layer (film), region, pad or patterns, it can be "directly on" the other element or substrate, or "intervening elements" may also be present. Further, it will be understood that when an element is referred to as being "under" another element, substrate, layer (film), region, pad or patterns, it can be "directly under", or "one or more intervening elements" may also be present. In the figures, the dimensions of elements and regions may be exaggerated, omitted or schematically illustrated for clarity of illustration. Hereinafter, the embodiments will be described with reference to the accompanying drawings.

Figure 2:
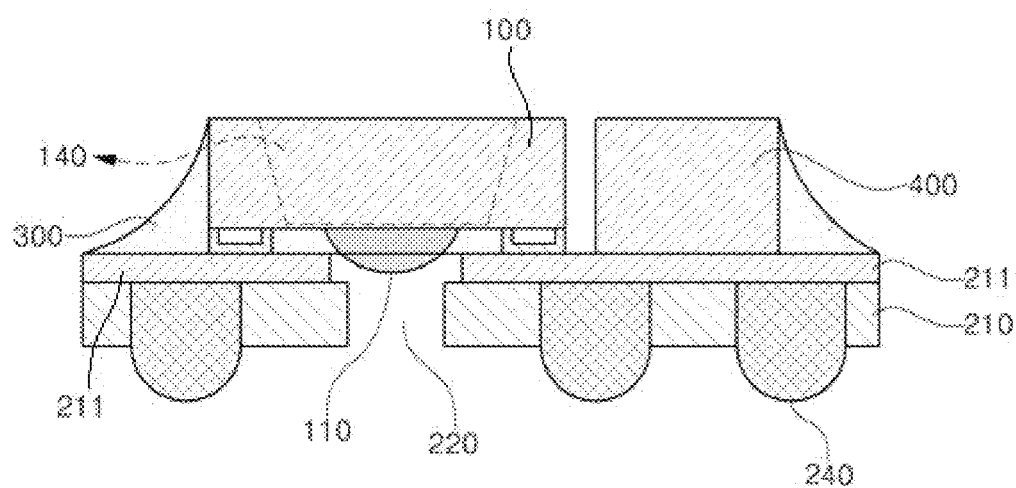
Figure 3:
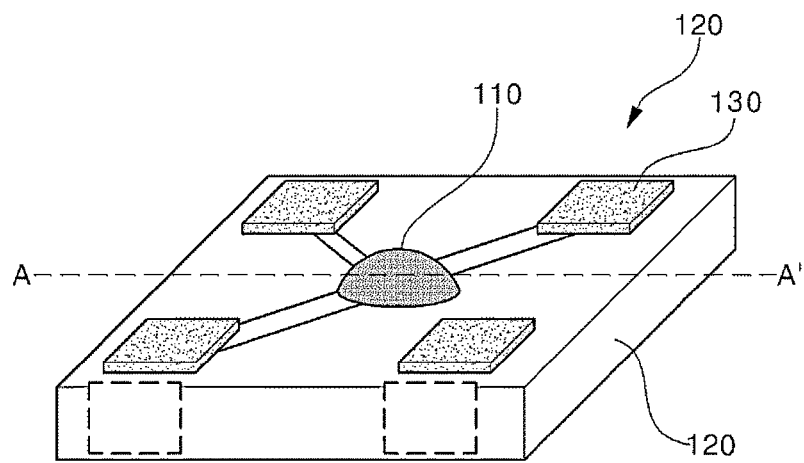
FIGS. 3 to 5 illustrate a gas sensing element according to an embodiment of the present application.

FIGS. 1 and 2 illustrate cross-sectional views of main portions of a gas sensing package according to an embodiment of the present application. FIG. 3 illustrates a conceptual view of main portions of a gas sensing element according to an embodiment of the present application.

Referring to FIGS. 1 to 3, the gas sensing package according to the embodiment of the present application includes: a first substrate 210 including a gas inflow hole 220; and a gas sensing element 100 mounted to the first substrate 210 and including a gas sensing portion 110, wherein the gas sensing portion 110 is mounted to face a surface of the first substrate.

As illustrated in FIG. 1, the first substrate 210 is configured such that metal patterns 211, 212 patterned with a metal material are included on the surface of the first substrate 210 made of an insulating material, and in particular, the first substrate includes the gas inflow hole 220 configured to pass through an upper part and a lower part of the first substrate 210.

The gas inflow hole 220 serves as a path for enabling gas to flow by exposing the gas sensing portion 110 of the gas sensing element 100.

Moreover, in addition to the gas inflow hole 220, the first substrate 210 has multiple through holes 230 for a combination of the first substrate 210 and an external substrate or an object, and in particular, each of the through holes 230 is filled with a metal material (hereinafter referred to as 'metal filling portion') as illustrated in FIGS. 1 and 2. As illustrated, the metal filling portion 240 is configured to protrude to a lower part of the first substrate 210 to the extent of a fixed portion. As such, as the metal filling portion 240 is configured to protrude, the metal filling portion 240 functions to provide a gas movement path while being electrically bonded to an object such as a printed circuit board, namely, a second substrate which will be described later.

Also, the metal patterns 211, 212 of an upper surface of the first substrate 210 are directly bonded to respective electrode pads 130 of the gas sensing element 100, and the metal patterns 211, 212 are generally formed in a structure in which a surface treatment plated layer of Ag, Au, Sn and the like is included in a Cu layer, so that a bonding ability with the electrode pads 130 can be improved.

In particular, each of the metal patterns 211, 212 is formed in a range of 1 μm hundreds of μm by adjusting a thickness thereof so as to enable gas to flow into a side part of the gas sensing element 100.

The gas sensing element 100 may include the gas sensing portion 110 intended for enabling gas sensing, and all gas sensing type structures, which have been commonly commercialized, may be applied as the gas sensing element. A sensing element using an oxide semiconductor, a sensing element using a carbon nanotube, various other sensing semiconductor chips and the like may be applied as the gas sensing element. In the embodiment of the present application, the gas sensing portion is characteristically mounted to face a surface of the first substrate 210 to which the gas sensing element 100 is mounted.

That is, the electrode pads 130 of the gas sensing element 100 are directly bonded to the respective metal patterns 211, 212 of the first substrate 210 using a flip chip bonding method so that a bonding wire can be removed. Thus, an area of the package can be reduced, and separate instruments such as a cap member, a mesh member and the like are not needed in an upper part of the gas sensing portion, thereby ensuring miniaturization of the package and a reduction in production costs.

As illustrated in FIGS. 1 and 2, it is preferable that the gas sensing portion 110 of the gas sensing element 100 being aligned to correspond to the gas inflow hole 220 of the first substrate 100 so as to come into contact with gas according to the movement of the gas from the outside. In terms of sensing efficiency, it is the most effective to align the gas sensing portion 110 to be exposed via the gas inflow hole 220 so that contact efficiency with gas can be increased, namely, to arrange the gas sensing portion 110 such that the gas sensing portion 110 is aligned with a center part of the gas inflow hole 220.

Of course, the present application is not limited thereto, and with regard to the alignment configuration, the gas sensing portion may be arranged to deviate from a center part of the gas inflow hole in a predetermined range. In this case, in the embodiment of the present application, in terms of the gas sensing element, gas detection may be supplemented by the gas inflow portion and the like, and thus the same effect of the improvement in sensing efficiency may be implemented.

Moreover, an output change portion 400 may be further included in the first substrate 210. The output change portion 400 may be composed of a fixed resistance element or an NTC (negative temperature coefficient) thermistor. In of the case of the fixed resistance element or the NTC (negative temperature coefficient) thermistor, a resistance mode is converted into the output of a voltage mode, and in particular, the NTC thermistor may have a predetermined initial voltage value by compensating an initial sensing material for a resistance change value according to each temperature.

Meanwhile, in the embodiment of FIGS. 1 and 2, a molding portion 300 is formed on the gas sensing element 100.

At this time, in the embodiment of FIG. 1, the molding portion 300 is formed to bury the gas sensing element 100 and an upper surface of the first substrate 210, and in the embodiment of FIG. 2, the molding portion 300 is applied to a side of the gas sensing element 100 and the first substrate 210 so that the gas sensing element 100 can be fixed to the first substrate 210.

According to the embodiment of FIG. 1, it is advantageous in that the molding portion 300 may be more stably formed to bury the gas sensing element 100, and according to the embodiment of FIG. 2, it is advantageous in that a size of the molding portion 300 may be minimized so that material costs can be minimized, the gas sensor package can become smaller, and the gas sensing element 100 can be efficiently fixed.

Figure 4:
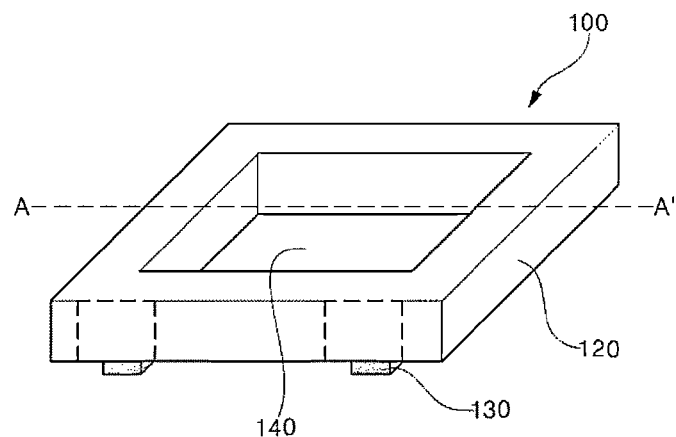
Figure 5:
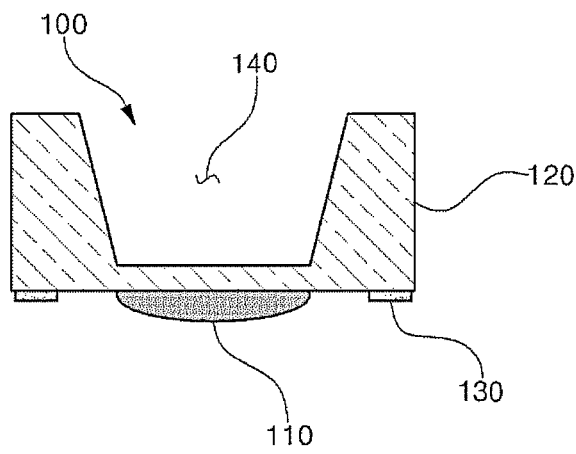

FIGS. 3 to 5 are conceptual views illustrating an implemented example of the gas sensing element according to the embodiment of the present application mounted to the gas sensing package described in the sections regarding FIGS. 1 and 2.

FIG. 3 is a perspective view of the gas sensing element 100 according to the embodiment of the present application and shows that the gas sensing portion 110 for detecting gas using a sensing material or a sensing chip is disposed on a surface of the body 120, and the electrode pads 130 connectable to an external terminal are provide on each adjacent surface, so the gas sensing portion 110 and the electrode pads 130 may be electrically connected to each other.

FIG. 4 illustrates a lower surface of the gas sensing element 100 according to the embodiment of the present application, and FIG. 5 illustrates a cross section of the gas sensing element 100 taken along lines A-A' of FIGS. 3 and 4.

As illustrated in FIGS. 4 and 5, a cavity portion 140 is formed inside the body 120 so that a gas residence time can be secured.

The gas sensing element 100 is mounted such that the gas sensing portion 110 faces the surface of the first substrate 210 in FIGS. 1 and 2, and in particular, the gas sensing element is mounted so that gas flowing through the gas inflow hole 220 of the first substrate 210 can be detected.

FIGS. 1 and 2 show a structure in which the gas sensing element 100 is mounted to the first substrate, and with regard to a structural difference, molding may be performed in such a manner as to maintain the cavity portion 140 by molding the gas sensing element, or the fixed resistance element or the NTC (negative temperature coefficient) thermistor using a high viscosity molding material such as epoxy and the like while maintaining the cavity portion 140 inside the gas sensing element 100.

At this time, when a low viscosity molding material is used, only peripheral portions except for an upper surface of the gas sensing element 100 or the fixed resistance element or the NTC (negative temperature coefficient) thermistor are molded and fixed so that the cavity portion 140 inside the gas sensing element 100 can be maintained, thereby enabling the improvement of sensing efficiency.

Unlike a cap member or a mesh member arranged at an upper part of the conventional sensing portion, the molding portion 300 is a fixing material for fixing the gas sensing element 100 itself, and has little effect on an increase in a size of the package because a size of the molding portion is very small.

Figure 6:
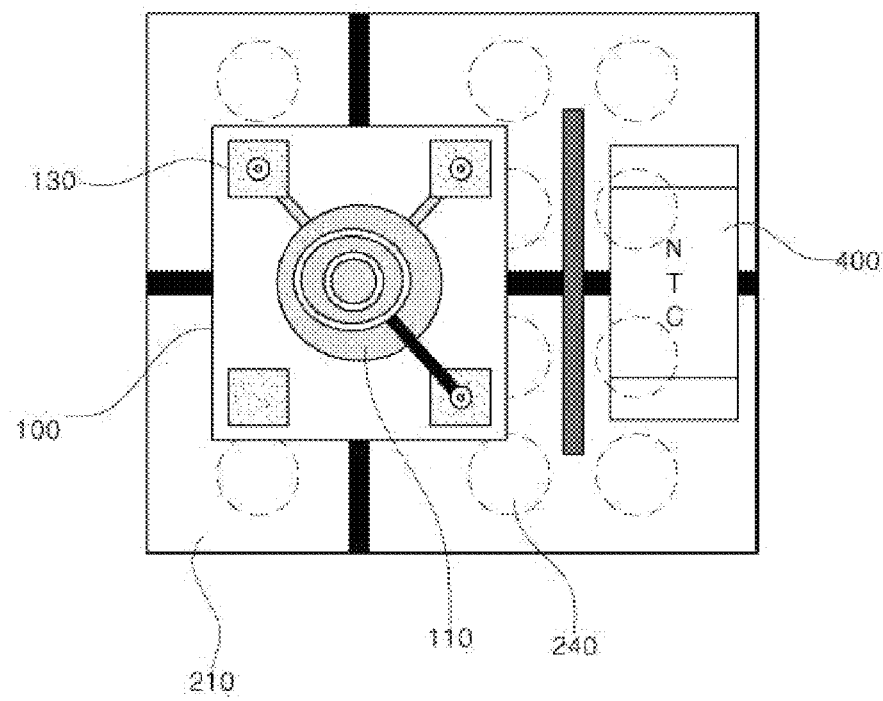
FIG. 6 is an upper plane view of the gas sensing package according to the embodiment of the present application.

FIG. 6 illustrates an upper plane view showing a state in which the gas sensing element 100 of FIGS. 1 and 2 is mounted to the first substrate 210.

As illustrated therein, the gas sensing portion 110 of the gas sensing element 100 is bonded onto the surface of the first substrate 210 using a flip chip method such that the gas sensing portion can face the surface of the first substrate.

The metal filling portions 240 may be disposed at a lower part of the first substrate 210 and the fixed resistance element or the NTC (negative temperature coefficient) thermistor 400 may be further included in the first substrate.

Figure 7:
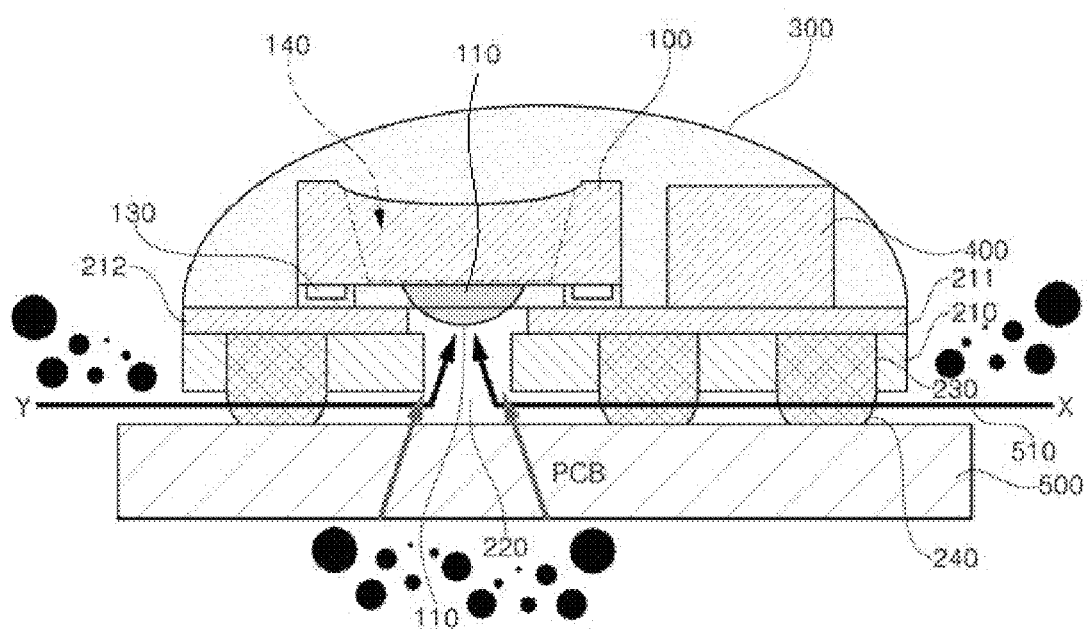
FIGS. 7 and 8 illustrate conceptual views in which gas sensing is implemented by combining the gas sensing package according to the embodiment of the present application with a printed circuit board (PCB)
Figure 8:
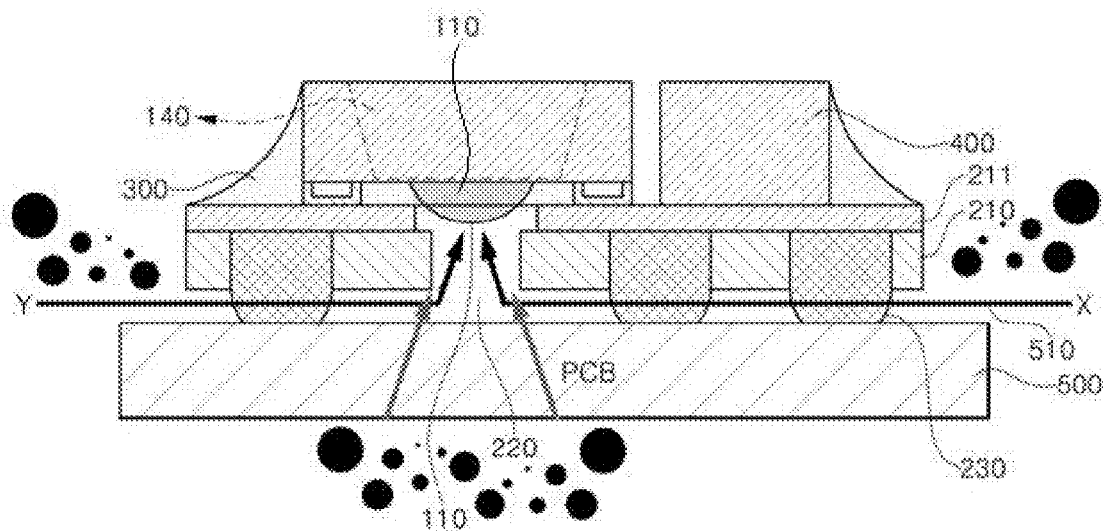

FIGS. 7 and 8 illustrate application examples of a structure in which the package according to the embodiment of FIGS. 1 and 2 is bonded to a second substrate 500.

According to FIGS. 7 and 8, a printed circuit board may be applied as the second substrate 500. In particular, the printed circuit board may be made of a flexible material, and as illustrated, the second substrate 500, which is the printed circuit board, is electrically connected to the metal filling portions 240 of the first substrate 210.

At this time, since the metal filling portions 240 protrude in a direction of a lower surface of the first substrate 210 to the extent of a predetermined part, a predetermined spaced portion 510 is formed even after the metal filling portions have been connected to the second substrate 500, and as illustrated, the spaced portion 510 forms a gas inflow portion 510 which is a gas movement path.

The gas inflow portion 510 enables gas to directly come into contact with the gas sensing portion 110 via the gas inflow hole 220 provided at the first substrate and also ensures an increase of sensing efficiency by enabling gas flowing from a side part of the gas sensing element 100 to come into contact with the gas sensing portion 110.

In order to ensure contact efficiency with gas, since the conventional gas sensors are implemented such that the gas sensing portion is disposed to face an upper surface of the substrate, the gas sensing portion should necessarily face the upper part of the substrate and a protective net in a mesh structure and the like are needed, and as a result, a size of each package may be necessarily increased. However, in the package according to the embodiment of the present application, since a part in which the gas sensing portion 110 is provided is implemented to be in contact with the surface of the first substrate 210, a separate cap is not installed so that the package can be miniaturized and production costs can be reduced. Furthermore, since the gas inflow portion 510 for guiding gas from the gas inflow hole 220 and the side of the gas sensing element to the gas sensing portion is implemented, sensing efficiency can be also ensured.

Figure 9:
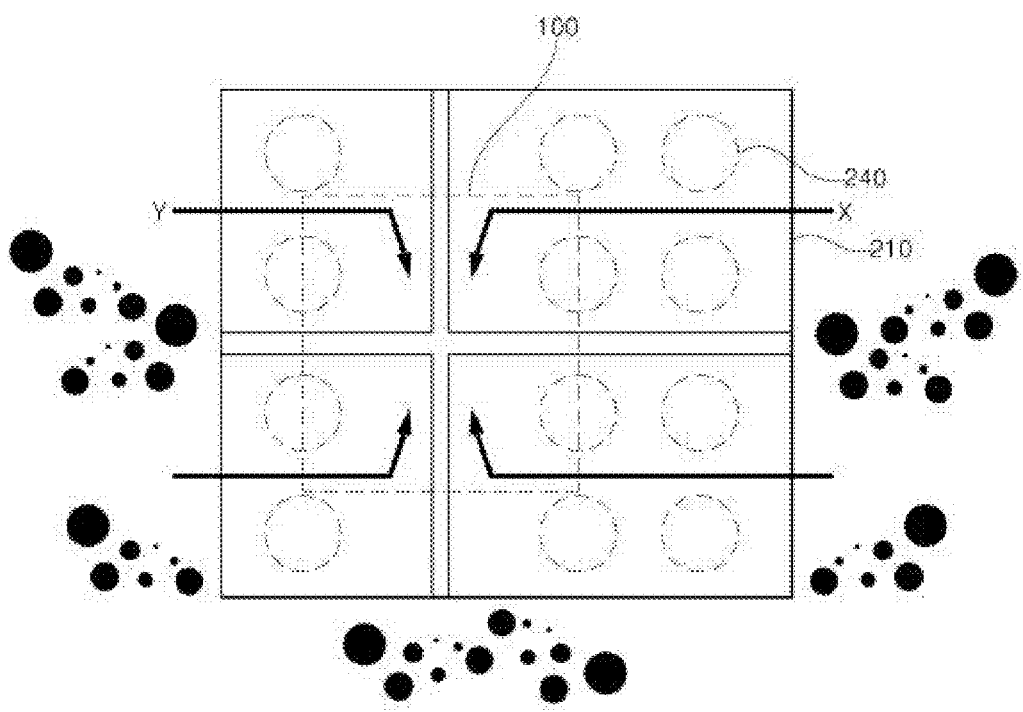
FIG. 9 is a conceptual view illustrating the transfer flow of air generated between the gas sensing package according to the embodiment of the present application and the PCB.

FIG. 9 is a plane concept view of the package of FIG. 8 as viewed from above and illustrates gas movement paths X, Y via the gas inflow portion 510 after the lower PCB 500 and the first substrate 210 have been connected to each other.

As illustrated therein, the smooth ventilation of gas flowing via the gas inflow portion 510 between the first substrate 210 and the lower PCB 500 from right and left sides as well as gas flowing from the lower part of the gas sensing element 100 is realized so that gas can be more easily transferred to the gas sensing portion 110.

Figure 10:
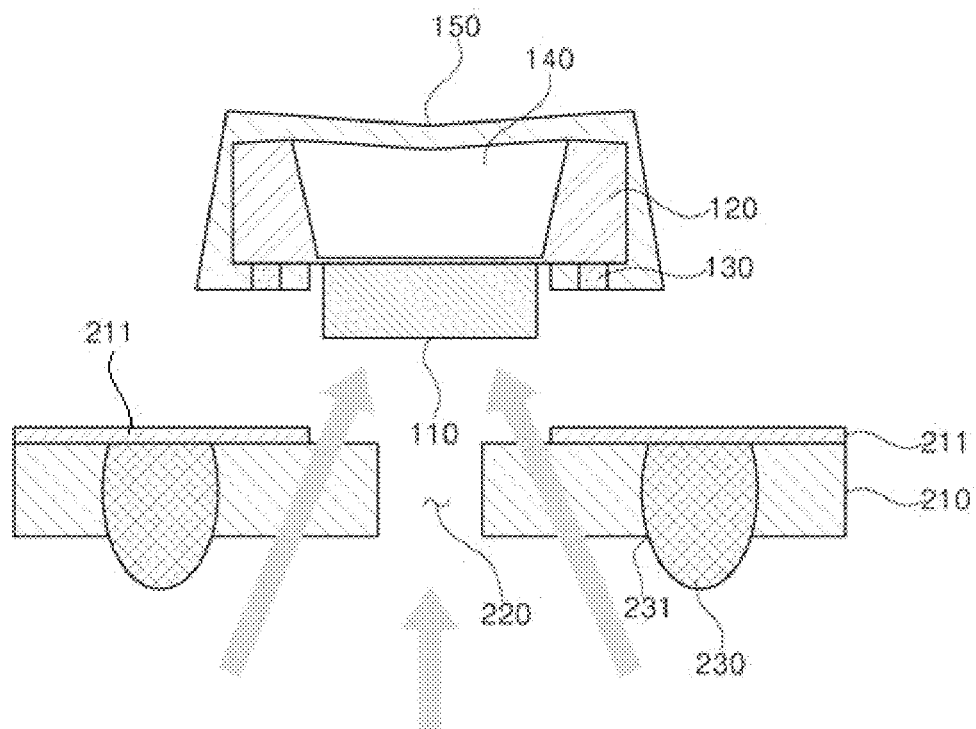
FIG. 10 illustrates a sectional concept view of the gas sensor package according to the embodiment of the present application.
Figure 11:
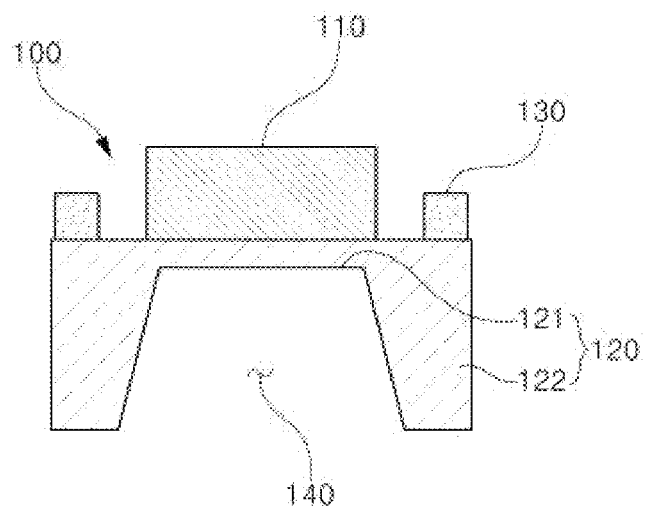
FIG. 11 illustrates a structure of the gas sensing element according to the embodiment of the present application mounted to the gas sensor package of FIG. 10.

FIG. 10 illustrates a sectional concept view of a gas sensor package according to the other embodiment of the present application, and FIG. 11 illustrates a structure of a gas sensing element according to the other embodiment of the present application mounted to the gas sensor package of FIG. 10.

Referring to FIGS. 10 and 11, the gas sensor package includes the first substrate 210 including the metal patterns and the gas inflow hole 220, and the gas sensing element 100 mounted to the metal patterns 211, 212, wherein the gas sensing portion 110 is disposed to correspond to the gas inflow hole 220.

The gas inflow hole 220 is a basic element which allows the gas sensor package to be implemented in a flip chip bonding method, and also enables an increase of sensing efficiency along with the cavity portion 140 inside the gas sensing element 100.

The gas sensing element 100 basically functions to detect gas and includes the gas sensing portion 110 including a sensing material for enabling gas sensing. All gas sensing type structures, which have been commonly commercialized, may be applied as the gas sensing element, namely, a sensing element using an oxide semiconductor, a sensing element using a carbon nanotube, various other sensing semiconductor chips and the like may be applied as the gas sensing element.

The electrode pads 130 of the gas sensing element 100 are directly bonded to the respective metal patterns 211, 212 of the first substrate 210 using a flip chip bonding method so that a bonding wire can be removed, thereby enabling a reduction in an area of the package. Furthermore, since a separate instrument such a cap member or a mesh member is not needed in the upper part of the gas sensing portion, the package can be more miniaturized, and the production costs can be reduced.

Specifically, as illustrated in FIG. 11, the gas sensing element 100 may include: the body 120 having a lower surface 121; a side wall 122 and the cavity portion 140; and the gas sensing portion 110 configured for sensing gas passing through the cavity portion 140 or the gas inflow hole 220 of the first substrate 210.

In particular, the body 120 may be configured such that the cavity 140 is formed and the gas sensing portion 110 is disposed on an opposite surface of the lower surface 121.

In order to increase gas sensing efficiency of the gas sensing portion 110, multiple communicating holes may be formed in the lower surface 121, and in the structure show in FIG. 10, by enabling gas passing through the gas inflow hole 220 to remain in the cavity portion 140, gas sensing efficiency can be improved.

At this time, if any element is made of a material having an insulating property, all elements may be applied as the first substrate 210. For example, PI, PET, PPG and the like may be applied.

Also, the metal filling portions 230, which protrude to the lower part of the first substrate 210 by filling through holes 231 with a metal material, may be formed on the first substrate 210.

Accordingly, when the second substrate such as the printed circuit board is additionally connected to the lower part of the first substrate 210, the first substrate 210 and the second substrate are separated from each other by the protruding metal filling portions 230 in a connection portion with the first substrate so that gas movement paths can be formed, and gas can freely move, thereby enabling higher gas sensing efficiency.

Also, the metal patterns 211, 212 of the upper surface of the first substrate 210 are directly bonded to the respective electrode pads 130 of the gas sensing element 100, and the metal patterns 211, 212 are generally formed in a structure in which a surface treatment plated layer of Ag, Au, Sn and the like is included in a Cu layer, so that a bonding ability with the electrode pads 130 can he improved.

In particular, each of the metal patterns 211, 212 is formed in a range of 1 μm ~hundreds of μm by adjusting a thickness thereof so as to enable gas to flow into a side part of the gas sensing element 100.

Also, in the embodiment of FIG. 10, the gas sensing portion 110 of the gas sensing element 100 may be aligned to correspond to the gas inflow hole 220 of the first substrate 100 so as to come into contact with gas according to the movement of the gas from the outside.

In terms of sensing efficiency, it is the most effective to align the gas sensing portion 110 to be exposed via the gas inflow hole 220, namely, to arrange the gas sensing portion 110 such that the gas sensing portion 110 is aligned with a center part of the gas inflow hole 220.

Of course, the present application is not limited thereto, and with regard to the alignment configuration, the gas sensing portion may be arranged to deviate from a center part of the gas inflow hole in a predetermined range. In this case, in the embodiment of the present application, in terms of the gas sensing element, gas detection may be supplemented by the gas inflow portion and the like, and thus the same effect of the improvement in sensing efficiency may be implemented.

Figure 12:
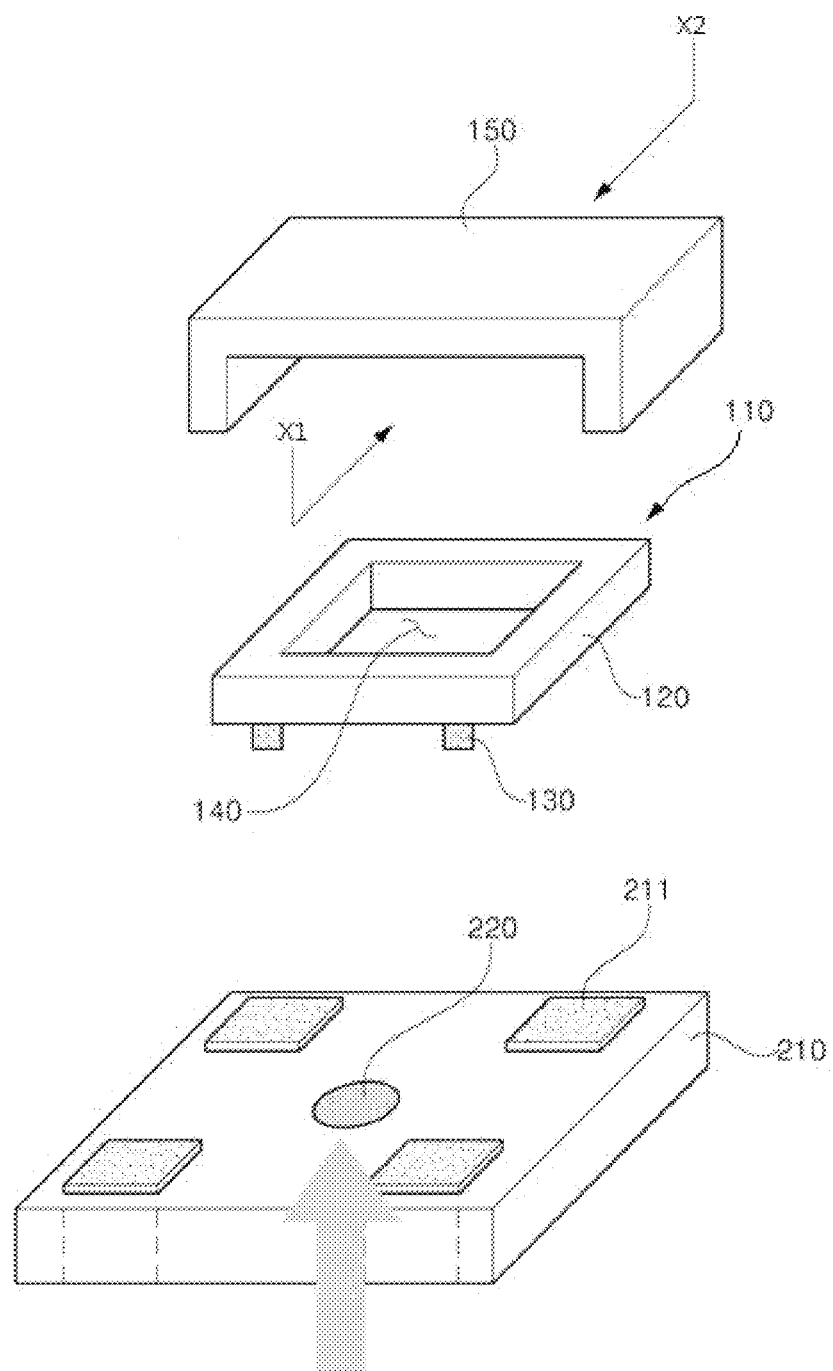
FIG. 12 is a conceptual view showing a combination for the gas sensor package according to the embodiment of FIG. 10.
Figure 13:
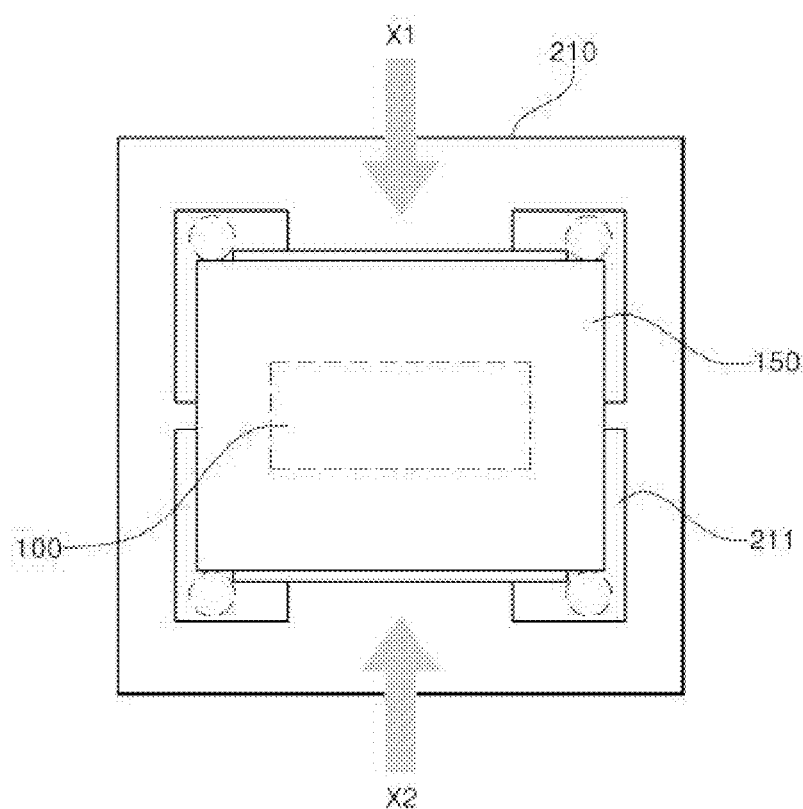
FIG. 13 is an upper plane view of the gas sensor package after the combination of FIG. 12.

FIG. 12 is a conceptual view showing a combination for the gas sensor package according to the embodiment of FIG. 10, and FIG. 13 is an upper plane view of the gas sensor package after the combination of FIG. 12.

Referring to FIGS. 12 and 13, the ventilation of gas is performed via the gas inflow hole 220 provided at the first substrate 210 so that the gas may enter from a lower part.

Also, the electrode pads 130 of the gas sensing element 100 are connected to the respective metal patterns 211, 212 provided on the surface of the first substrate 210 so that a connection between the gas sensing element 100 and the first substrate 210 can be realized in a flip chip bonding method.

The cavity portion is formed inside the body 120 of the gas sensing element 100 so that a structure in which an upper part of the body is open can be implemented, and as illustrated, the protective portion 150 using a molding material may be connected to the upper part of the body of the gas sensing element 100.

Various molding material may be applied as the protective portion 150, and the protective portion may be formed to surround the gas sensing element 100 by using, for example, a high viscosity molding material such as epoxy and the like. In this case, in particular, as illustrated in FIGS. 12 and 13, a shape of the protective portion 150 is formed in a structure X1, X2 in which a part or an entire part of the side thereof is open, so that gas in the side can freely move.

In a case where the protective portion 150 is formed using a molding material, only peripheral portions except for the upper surface of the gas sensing element 100 are molded and fixed even in the case in which a low viscosity molding material is applied, as well as a case in which a high viscosity molding material is applied, and accordingly, the cavity portion inside the gas sensing element 100 is maintained, thereby enabling the improvement of gas sensing efficiency.

As set forth above, according to the embodiments of the present application, since the gas sensing element is mounted in a flip chip bonding method so as to perform sensing via the gas inflow hole formed in the substrate so that the gas sensor can be formed in a very slim structure.

In particular, it is advantageous in that wire bonding is not needed because the gas sensing element is directly mounted to the metal electrode of the substrate, so that an area of the package can be reduced, and an entire height of the package can be also reduced.

Also, unlike the conventional gas sensor packages, a separate cap for protecting the gas sensing portion of the upper part of the sensor chips is not needed so that the production costs can be more reduced, and the package can be more miniaturized.

Moreover, it is advantageous in that gas can enter through the space portion of the side of the chips in addition to primarily entering through gas inflow hole of the substrate as gas paths for sensing, so that efficient sensing can be realized.

Based on slim structure and multifunction as described above, the gas sensor package according to various embodiments of the present application can be applied to general IT devices in which a reduction in an entire size of the package and a reduction of the production costs are reflected.

As previously described, in the detailed description of the invention, having described the detailed exemplary embodiments of the invention, it should be apparent that modifications and variations can be made by persons skilled without deviating from the spirit or scope of the invention. Therefore, it is to be understood that the foregoing is illustrative of the present application and is not to be construed as limited to the specific embodiments disclosed, and that modifications to the disclosed embodiments, as well as other embodiments, are intended to be included within the scope of the appended claims and their equivalents.

The present application has been made keeping in mind the above problems, an aspect of embodiments of the present application provides a gas sensor package capable of constituting a gas sensor having a slim structure by mounting a gas sensing element to a substrate using a flip chip bonding method to enable sensing to be performed via a gas inflow hole formed on the substrate.

According to an aspect of an embodiment of the present application, there is provided a gas sensor package including: a first substrate including a gas inflow hole; and a gas sensing element mounted to the first substrate and including a gas sensing portion disposed to correspond to the gas inflow hole.

According to another embodiment of the present application, the gas inflow hole may be formed to pass through the first substrate.

According to still another embodiment of the present application, the first substrate may further include metal patterns, and the gas sensing element may be bonded to the metal patterns.

According to still another embodiment of the present application, the gas sensing package may further include metal filling portions connected to the respective metal patterns by passing through the first substrate.

According to still another embodiment of the present application, each of the metal filling portions may protrude from a surface of the first substrate.

According to still another embodiment of the present application, the gas sensor package may further include a second substrate connected to the first substrate via the metal filling portions.

According to still another embodiment of the present application, the gas sensor package may further include a gas inflow portion between the first substrate and the second substrate to communicate with the gas inflow hole.

According to still another embodiment of the present application, the gas sensor package may further include an output change portion mounted to the first substrate to change an output mode of the gas sensing element.

According to still another embodiment of the present application, the output change portion may be composed of a fixed resistance element or an NTC (Negative Temperature Coefficient) thermistor.

According to still another embodiment of the present application, the gas sensor package may further include a molding portion formed on the gas sensing element.

According to still another embodiment of the present application, the molding portion may formed to bury the gas sensing element and an upper surface of the first substrate.

According to still another embodiment of the present application, the molding portion may be applied to a side of the gas sensing element and the first substrate so as to enable the gas sensing element to be fixed to the first substrate.

According to still another embodiment of the present application, the gas sensor package may further include a protective portion bonded to the gas sensing element to cover the gas sensing element.

According to still another embodiment of the present application, the gas sensing element may include a body having a cavity portion for enabling gas to enter via the gas inflow hole; and a gas sensing portion for sensing the gas.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A gas sensor package, comprising:
   a first substrate including a gas inflow hole and metal patterns;
   a gas sensing element mounted to the first substrate and including a gas sensing portion provided to correspond to the gas inflow hole and bonded to the metal patterns;
   metal filling portions connected to respective metal patterns of the first substrate, each of the metal filling portions protruding from a surface of the first substrate and passing through the first substrate;
   a second substrate, wherein each of the metal filling portions contacts the second substrate to connect the second substrate to the first substrate; and
   an output change portion mounted on the first substrate to change an output mode of the gas sensing element.

2. The gas sensor package of claim 1, wherein the gas inflow hole passes through the first substrate,
   wherein the output change portion is a fixed resistance element or an NTC (Negative Temperature Coefficient) thermistor.

3. The gas sensor package of claim 1, further comprising a gas inflow portion formed between the first substrate and the second substrate to communicate with the gas inflow hole.

4. The gas sensor package of claim 1, further comprising a molding portion formed on the gas sensing element, wherein the molding portion is applied to a side of the gas sensing element and the first substrate so as to enable the gas sensing element to he fixed to the first substrate.

5. The gas sensor package of claim 1, wherein the gas sensing element includes: a body in which a cavity portion is formed such that an upper part of the body is open; and a protective portion bonded to the gas sensing element to cover the upper part of the body of the gas sensing element.

6. The gas sensor package of claim 5, wherein at least a part of the side of the protective portion is open so that gas can move.

7. A gas sensor package, comprising:
   a first substrate including a gas inflow hole;
   a gas sensing element mounted to the first substrate and including a gas sensing portion provided to correspond to the gas inflow hole; and
   an output change portion mounted on the first substrate to change an output mode of the gas sensing element.

8. The gas sensor package of claim 7, wherein the output change portion is a fixed resistance element or an NTC (Negative Temperature Coefficient) thermistor.

9. A gas sensor package, comprising:
   a first substrate including a gas inflow hole;
   a gas sensing element mounted to the first substrate and including a gas sensing portion provided to correspond to the gas inflow hole; and
   a molding portion formed on the gas sensing element, wherein the molding portion is formed to bury the gas sensing element and an upper surface of the first substrate.

* * * * *